US008287755B2

(12) United States Patent
Smith et al.

(10) Patent No.: US 8,287,755 B2
(45) Date of Patent: Oct. 16, 2012

(54) SOLID-LAYERED BLEACH COMPOSITIONS

(75) Inventors: William L. Smith, Pleasanton, CA (US); Evan M. Rumberger, San Francisco, CA (US)

(73) Assignee: The Clorox Company, Oakland, CA (US)

( * ) Notice: Subject to any disclaimer, the term of this patent is extended or adjusted under 35 U.S.C. 154(b) by 519 days.

(21) Appl. No.: 12/620,932

(22) Filed: Nov. 18, 2009

(65) Prior Publication Data

US 2010/0140544 A1 Jun. 10, 2010

Related U.S. Application Data

(60) Provisional application No. 61/121,029, filed on Dec. 9, 2008.

(51) Int. Cl.
*C01B 11/06* (2006.01)
*A61Q 11/02* (2006.01)
*A61Q 11/00* (2006.01)
*A61K 8/20* (2006.01)

(52) U.S. Cl. ......... 252/187.27; 252/187.28; 252/187.29; 252/187.3; 252/186.37; 510/116; 510/117; 510/298; 510/302; 510/349; 510/380; 510/446; 422/28; 422/29

(58) Field of Classification Search ............. 252/187.27, 252/187.28, 187.29, 187.3, 186.37; 510/116, 510/117, 298, 302, 349, 380, 446; 422/28, 422/29

See application file for complete search history.

(56) References Cited

U.S. PATENT DOCUMENTS 1,471,987 A 10/1923 Vogt
1,481,003 A * 1/1924 Gegenheimer ........... 252/186.37
1,961,576 A * 6/1934 Taylor ...................... 252/186.37
2,320,279 A 3/1938 Kalusdian
2,409,718 A 11/1941 Snell et al.
2,498,344 A 2/1950 Rider at al.
3,113,111 A 9/1959 Myerson
2,921,911 A 1/1960 Staubley
3,257,450 A 6/1966 Globus
3,337,466 A 8/1967 Puetzer et al.
3,342,674 A * 9/1967 Kowalski ...................... 424/661
3,446,893 A * 5/1969 Hanford et al. ............. 424/76.3
3,640,879 A 2/1972 Fitzgerald, Jr.
3,755,179 A 8/1973 Fitzgerald, Jr.
3,769,224 A * 10/1973 Inamorato ..................... 510/302
3,793,211 A 2/1974 Kohlhepp et al.
3,821,117 A 6/1974 Breece et al.
3,936,385 A 2/1976 Cheng
4,035,484 A * 7/1977 Faust et al. .................... 424/665
RE29,473 E 11/1977 Fitzgerald, Jr.
4,082,841 A 4/1978 Pader
4,087,360 A * 5/1978 Faust et al. .................... 210/701
4,146,676 A 3/1979 Saeman
4,256,599 A * 3/1981 Krisp et al. ................... 510/117
4,276,349 A 6/1981 Saeman
4,362,639 A 12/1982 Eoga
4,421,664 A 12/1983 Anderson et al.
4,552,679 A 11/1985 Schobel et al.
4,657,784 A 4/1987 Olson
4,671,972 A * 6/1987 Schobel et al. ............... 427/213
4,692,335 A 9/1987 Iwanski
4,707,160 A 11/1987 Chun et al.
4,731,195 A 3/1988 Olson
4,933,102 A 6/1990 Olson
4,961,872 A 10/1990 Sinclair
5,114,647 A 5/1992 Levesque et al.
5,133,892 A 7/1992 Chun et al.
5,407,598 A * 4/1995 Olson et al. .............. 252/186.35
5,534,178 A 7/1996 Bailly et al.
5,599,781 A 2/1997 Haeggberg et al.
5,753,602 A 5/1998 Hung
5,869,438 A 2/1999 Svendsen et al.
5,981,457 A 11/1999 Ahmed
6,071,539 A * 6/2000 Robinson et al. ............. 424/466
6,146,538 A * 11/2000 Martin .......................... 210/698
6,211,129 B1 4/2001 Gladfelter et al.
6,298,871 B1 * 10/2001 Pickens et al. ................ 137/268
6,358,909 B1 3/2002 Ochomogo
6,426,111 B1 * 7/2002 Hirsch .......................... 426/590
6,468,950 B1 10/2002 Kawasaki et al.
6,589,443 B1 * 7/2003 Olson et al. ................ 252/186.2
6,852,238 B2 2/2005 Connelly, Jr.
6,863,830 B1 3/2005 Purdy
6,969,527 B2 11/2005 Brennan (Continued)

FOREIGN PATENT DOCUMENTS

GB 490384 8/1938

(Continued)

OTHER PUBLICATIONS

International Search Report of PCT Application No. PCT/US2009/065090, Jan. 21, 2010, 3 Pages.

Written Opinion of PCT Application No. PCT/US2009/065090, Jan. 21, 2010, 5 Pages.

International Search Report of PCT Application No. PCT/US10/52487, Jan. 4, 2011, 3 Pages.

International Search Report of PCT Application No. PCT/US10/56117, Jan. 14, 2011, 3 Pages.

International Search Report of PCT Application No. PCT/US10/56139, Jan. 18, 2011, 3 Pages.

*Primary Examiner* — Joseph D Anthony

(74) *Attorney, Agent, or Firm* — Alok Goel; Stacy H. Combs

(57) ABSTRACT

The present invention provides a solid-layered composition having at least two parts. The first part comprises a) calcium hypochlorite, magnesium hypochlorite and mixtures thereof, b) a builder, c) a water-soluble polymer, d) an acid, and e) wherein the first part does not contain sodium hypochlorite, lithium hypochlorite, potassium hypochlorite and mixtures thereof. The second part comprises a) a surfactant, b) a builder, c) an acid, and d) wherein the second part does not contain any oxidant.

20 Claims, No Drawings

U.S. PATENT DOCUMENTS

| | | | | |
|---|---|---|---|---|
| 6,995,129 | B2 | 2/2006 | Olson | |
| 7,309,444 | B2 * | 12/2007 | Connelly, Jr. | 210/753 |
| 7,410,938 | B2 | 8/2008 | Brennan | |
| 7,517,413 | B2 | 4/2009 | van Buskirk et al. | |
| 2002/0189634 | A1 | 12/2002 | Vanhauwermeiren et al. | |
| 2002/0198128 | A1 | 12/2002 | Perkins et al. | |
| 2003/0086878 | A1 * | 5/2003 | Rajaiah et al. | 424/49 |
| 2004/0081690 | A1 * | 4/2004 | Gauthier et al. | 424/465 |
| 2004/0082491 | A1 * | 4/2004 | Olson et al. | 510/375 |
| 2004/0266650 | A1 | 12/2004 | Lambotte et al. | |
| 2005/0143274 | A1 | 6/2005 | Ghosh et al. | |
| 2005/0233900 | A1 | 10/2005 | Smith et al. | |
| 2005/0288209 | A1 | 12/2005 | Fletcher | |
| 2006/0258553 | A1 | 11/2006 | Catalfamo et al. | |
| 2008/0083071 | A1 * | 4/2008 | Tremblay et al. | 8/109 |
| 2008/0166176 | A1 | 7/2008 | Rees et al. | |
| 2009/0042756 | A1 | 2/2009 | Muzik et al. | |
| 2009/0148342 | A1 | 6/2009 | Bromberg et al. | |
| 2009/0165818 | A1 | 7/2009 | Smith et al. | |
| 2010/0140544 | A1 | 6/2010 | Smith et al. | |

FOREIGN PATENT DOCUMENTS

| | | |
|---|---|---|
| GB | 550020 | 12/1942 |
| GB | 552803 | 4/1943 |
| GB | 606431 | 8/1948 |
| GB | 739046 | 10/1955 |
| WO | WO 01/36115 | 5/2001 |
| WO | WO2010/077468 | 7/2010 |

* cited by examiner

SOLID-LAYERED BLEACH COMPOSITIONS

CROSS-REFERENCES TO RELATED APPLICATIONS

This application claims priority to U.S. Provisional Application No. 61/121,029, filed on Dec. 9, 2008, which is incorporated herein by reference.

BACKGROUND OF THE INVENTION

1. Field of the Invention

The present invention relates generally to solid-layered bleach compositions. These bleach compositions are used to clean and disinfect soft and hard surfaces.

2. Description of the Related Art

Solid bleach compositions have progressed for decades and created a large chemical industry devoted to cleaning and disinfecting hard surfaces and soft surfaces. N-Chloro hydantoins, N-chloro isocyanurates, sodium hypochlorite, and calcium hypochlorite are used quite frequently in bleach compositions for many companies because they are cheap to produce and they are highly effective. However, these bleach compositions have several disadvantages that limit their usefulness. Sodium hypochlorite is only available as a liquid at room temperature. Calcium hypochlorite leaves residue. Chlorinated hydantoins and isocyanurates lack long term solution stability and generate malodor. All these disadvantages present compositions which consumers may not prefer.

The presently claimed invention solves some of these problems. Use of calcium hypochlorite in at least a two-part system does not leave residues that are associated with other calcium hypochlorite compositions, nor do they generate malodors typically associated with the use of chlorinated isocyanurates. The present invention also releases bleach faster than the typical use of halogenated hydantoins. The present invention also dissolves faster than typical commercial products based on calcium hypochlorite or halogenated hydantoins. It is therefore an object of the present invention to provide a solid-layered bleach composition that overcomes the disadvantages and shortcomings associated with prior art solid bleach compositions.

SUMMARY OF THE INVENTION

In accordance with the above objects and those that will be mentioned and will become apparent below, one aspect of the present invention comprises a solid-layered bleach composition having at least two parts comprising a first part and a second part: wherein said first part comprises, a) 0.1%-50% of a hypochlorite selected from the group consisting of calcium hypochlorite, magnesium hypochlorite and mixtures thereof b) 20%-60% of a builder selected from carbonate, bicarbonate, sesquicarbonate and mixtures thereof c) 0.1%-60% of a water-soluble polymer, wherein said water-soluble polymer is selected from the group consisting of a polycarboxylate, sulfonated carboxylate, polysulfonate, polyvinylpyrrolidone, copolymers and mixtures thereof d) 1%-50% of an acid selected from the group consisting of sulfonic acid, dicarboxylic acid, monocarboxylic acid, aminocarboxylic acid and mixtures thereof e) optionally, fillers, desiccants, solid processing aids, colorants, a water-swellable polymer wherein said water-swellable polymer is selected from the group consisting of cross-linked polycarboxylate, cross-linked polysulfonate, cross-linked carboxymethyl cellulose, cellulose, sodium carboxymethylcellulose, and mixtures thereof and f) wherein said first part does not contain sodium hypochlorite, lithium hypochlorite, potassium hypochlorite, hydantoins, isocyanurates, carboxylic acids that have one or more hydroxyl group moieties, aliphatic or aromatic amines that possess a covalently bound proton to the nitrogen moiety, and mixtures thereof and wherein said second part comprises, a) 0.01%-25% of a surfactant selected from the group consisting of anionic, cationic, nonionic, amphoteric, zwitterionic and mixtures thereof b) 10-90% of a builder selected from carbonate, bicarbonate, sesquicarbonate and mixtures thereof c) 1-50% of an acid selected from the group consisting of sulfonic acid, dicarboxylic acid, monocarboxylic acid, aminocarboxylic acid and mixtures thereof d) optionally dyes, fillers, desiccants, solid processing aids, fragrances, preservatives, colorants, anti-corrosion inhibitors, and mixtures thereof and e) wherein said second part does not contain any oxidant wherein said oxidant comprises hypochlorite, N-halo compound, peracid, peroxide, peroxygen bleach and mixtures thereof.

In accordance with the above objects and those that will be mentioned and will become apparent below, another aspect of the present invention comprises a solid-layered bleach composition having at least two parts consisting essentially of a first part and a second part: wherein said first part consisting essentially of, a) 0.1%-50% of a hypochlorite selected calcium hypochlorite, magnesium hypochlorite and mixtures thereof; b) 20%-60% of a builder selected from carbonate, bicarbonate, sesquicarbonate and mixtures thereof; c) 0.1%-60% of a water-soluble polymer, wherein said water-soluble polymer is selected from the group consisting of a polycarboxylate, sulfonated carboxylate, polysulfonate, polyvinylpyrrolidone, copolymers and mixtures thereof; d) 1%-50% of an acid selected from the group consisting of sulfonic acid, dicarboxylic acid, monocarboxylic acid, aminocarboxylic acid and mixtures thereof; e) optionally, fillers, desiccants, solid processing aids, colorants, a water-swellable polymer wherein said water-swellable polymer is selected from the group consisting of cross-linked polycarboxylate, cross-linked polysulfonate, cross-linked carboxymethyl cellulose, cellulose, sodium carboxymethylcellulose and mixtures thereof; and f) wherein said first part does not contain sodium hypochlorite, lithium hypochlorite, potassium hypochlorite, hydantoins, isocyanurates, carboxylic acids that have one or more hydroxyl group moieties, aliphatic or aromatic amines that possess a covalently bound proton to the nitrogen moiety, and mixtures thereof; and wherein said second part consisting essentially of, a) 0.01-25% of a surfactant selected from the group consisting of anionic, cationic, nonionic, amphoteric, zwitterionic and mixtures thereof; b) 10-90% of a builder selected from the group consisting of carbonate, bicarbonate, sesquicarbonate and mixtures thereof; c) 1-50% of an acid selected from the group consisting of sulfonic acid, dicarboxylic acid, monocarboxylic acid, aminocarboxylic acid, and mixtures thereof; d) optionally a water-soluble polymer, wherein said water-soluble polymer is selected from the group consisting of polycarboxylate, sulfonated carboxylate, polysulfonate, polyvinylpyrrolidone, copolymers and mixtures thereof; e) optionally, a water-swellable polymer is selected from the group consisting of cross-linked polycarboxylate, cross-linked sulfonate, cross-linked carboxymethyl cellulose, cellulose, sodium carboxymethylcellulose, and mixtures thereof; f) optionally dyes, fillers, desiccants, solid processing aids, fragrances, preservatives, colorants, anti-corrosion inhibitors, and mixtures thereof; and g) wherein said second part does not contain any oxidant wherein said oxidant comprises hypochlorite, N-halo compound, peracid, peroxide, peroxygen bleach and mixtures thereof.

In accordance with the above objects and those that will be mentioned and will become apparent below, another aspect of the present invention comprising a solid-layered bleach composition having at least two parts consisting of a first part and a second part: wherein said first part consisting of, a) 0.1%-50% of a hypochlorite selected calcium hypochlorite, magnesium hypochlorite and mixtures thereof b) 20%-60% of a builder selected from carbonate, bicarbonate, sesquicarbonate and mixtures thereof c) 0.1%-60% of a water-soluble polymer, wherein said water-soluble polymer is selected from the group consisting of a polycarboxylate, sulfonated carboxylate, polysulfonate, polyvinylpyrrolidone, copolymers and mixtures thereof d) optionally, fillers, desiccants, solid processing aids, colorants, a water-swellable polymer wherein said water-swellable polymer is selected from the group consisting of cross-linked polycarboxylate, cross-linked polysulfonate, cross-linked carboxymethyl cellulose, cellulose, sodium carboxymethylcellulose, and mixtures thereof and e) wherein said first part does not contain sodium hypochlorite, lithium hypochlorite, potassium hypochlorite, hydantoins, isocyanurates, carboxylic acids that have one or more hydroxyl group moieties, aliphatic or aromatic amines that possess a covalently bound proton to the nitrogen moiety, and mixtures thereof and wherein said second part consisting of, a) 0.01%-25% of a surfactant selected from the group consisting of anionic, cationic, nonionic, amphoteric, zwitterionic and mixtures thereof b) 10%-90% of a builder selected from carbonate, bicarbonate, sesquicarbonate and mixtures thereof c) optionally dyes, fillers, desiccants, solid processing aids, fragrances, preservatives, colorants, anti-corrosion-inhibitors, a water-swellable polymer wherein said water-swellable polymer is selected from the group consisting of cross-linked polycarboxylate, cross-linked polysulfonate, cross-linked carboxymethyl cellulose, cellulose, sodium carboxymethylcellulose and mixtures thereof and d) wherein said second part does not contain an oxidant wherein said oxidant comprises hypochlorite, N-halo compound, peroxygen bleach and mixtures thereof.

Further features and advantages of the present invention will become apparent to those of ordinary skill in the art in view of the detailed description of preferred embodiments below, when considered together with the attached claims.

DETAILED DESCRIPTION OF THE INVENTION

Before describing the present invention in detail, it is to be understood that this invention is not limited to particularly exemplified systems or process parameters that may, of course, vary. It is also to be understood that the terminology used herein is for the purpose of describing particular embodiments of the invention only, and is not intended to limit the scope of the invention in any manner.

All publications, patents and patent applications cited herein, whether supra or infra, are hereby incorporated by reference in their entirety to the same extent as if each individual publication, patent or patent application was specifically and individually indicated to be incorporated by reference.

It must be noted that, as used in this specification and the appended claims, the singular forms "a," "an" and "the" include plural referents unless the content clearly dictates otherwise.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In the application, effective amounts are generally those amounts listed as the ranges or levels of ingredients in the descriptions, which follow hereto. Unless otherwise stated, amounts listed in percentage ("%'s") are in weight percent (based on 100% active) of the cleaning composition alone, not accounting for the substrate weight. Each of the noted cleaner composition components and substrates is discussed in detail below. Additionally, this application also covers methods steps of utilizing the compositions described in the present invention.

The term "comprising", which is synonymous with "including," "containing," or "characterized by," is inclusive or open-ended and does not exclude additional, unrecited elements or method steps. See MPEP 2111.03. See, e.g., *Mars Inc.* v. *H.J. Heinz Co.,* 377 F.3d 1369, 1376, 71 USPQ2d 1837, 1843 (Fed. Cir. 2004) ("like the term 'comprising,' the terms 'containing' and 'mixture' are open-ended."). *Invitrogen Corp.* v. *Biocrest Mfg., L.P.,* 327 F.3d 1364, 1368, 66 USPQ2d 1631, 1634 (Fed. Cir. 2003) ("The transition 'comprising' in a method claim indicates that the claim is open-ended and allows for additional steps."); *Genentech, Inc.* v. *Chiron Corp.,* 112 F.3d 495, 501, 42 USPQ2d 1608, 1613 (Fed. Cir. 1997) See MPEP 2111.03. ("Comprising" is a term of art used in claim language which means that the named elements are essential, but other elements may be added and still form a construct within the scope of the claim.); *Moleculon Research Corp.* v. *CBS, Inc.,* 793 F.2d 1261, 229 USPQ 805 (Fed. Cir. 1986); *In re Baxter,* 656 F.2d 679, 686, 210 USPQ 795, 803 (CCPA 1981); *Ex parte Davis,* 80 USPQ 448, 450 (Bd. App. 1948). See MPEP 2111.03.

The term "consisting essentially of" as used herein, limits the scope of a claim to the specified materials or steps "and those that do not materially affect the basic and novel characteristic(s)" of the claimed invention. *In re Herz,* 537 F.2d 549, 551-52, 190 USPQ 461, 463 (CCPA 1976) (emphasis in original). See MPEP 2111.03.

The term "consisting of" as used herein, excludes any element, step, or ingredient not specified in the claim. *In re Gray* 53 F.2d 520, 11 USPQ 255 (CCPA 1931); *Ex Parte Davis,* 80 USPQ 448, 450 (Bd. App. 1948). See MPEP 2111.03.

The term "cleaning composition", as used herein, is meant to mean and include a cleaning formulation having at least one surfactant.

The term "laundry composition", as used herein, is meant to mean and include a laundry formulation having at least one surfactant.

The term "surfactant", as used herein, is meant to mean and include a substance or compound that reduces surface tension when dissolved in water or water solutions, or that reduces interfacial tension between two liquids, or between a liquid and a solid. The term "surfactant" thus includes anionic, nonionic, cationic, zwiterrionic and/or amphoteric agents.

General

The present invention is directed to a solid-layered composition comprising at least two parts. The solid-layered composition may optionally have a third part. If a third part is present, the third part is situated between the first and second parts. The present invention does not work with a liquid composition. The first part of the solid-layered composition comprises at least calcium hypochlorite, magnesium hypochlorite or mixtures thereof. The second part of the solid-layered composition comprises at least one surfactant.

Optional ingredients may be added to either part to enhance the efficacy of the solid-layered composition.

Oxidants

The first part of the solid-layered composition can contain only calcium hypochlorite, magnesium hypochlorite or mixtures thereof. The first part of the solid-layered composition does not contain any other types of hypochlorite such as sodium hypochlorite, lithium hypochlorite, or potassium hypochorite. Therefore, the first part of the solid-layered composition does not contain any of the following compounds: hypobromites, hypoiodites, chlorinated trisodium phosphate dodecahydrates, potassium and sodium dichloroisocyanurates, trichlorocyanuric acid, N-chloroimides, N-chloroamides, N-chlorosulfamide, N-chloroamines, chlorohydantoins such as dichlorodimethyl hydantoin and chlorobromo dimethylhydantoin, bromo-compounds corresponding to the chloro-compounds above.

The second part of the solid-layered composition does not contain any oxidant. Oxidants, when used, include, but are not limited to, hypohalite (including any hypochlorite species), peracids, N-halo compound, hydrogen peroxide, and/or sources of hydrogen peroxide. Therefore, the second part of the solid-layered composition cannot contain an oxygen bleach, including a peroxygen, peroxyhydrate or active oxygen generating compound. As used herein a source of hydrogen peroxide refers to any compound which generates active oxygen when said compound is in contact with water. Therefore, the second part of the solid-layered composition cannot contain percarbonates, perborates, preformed percarboxylic acids, persilicates, persulphates, organic and inorganic peroxides and/or hydroperoxides. Additionally, the second part of the solid-layered composition does not contain the following compounds: hypochlorites, hypobromites, hypoiodites, hypochlorous, acids, chlorinated trisodium phosphate dodecahydrates, potassium and sodium dichloroisocyanurates, trichlorocyanuric acid, N-chloroimides, N-chloroamides, N-chlorosulfamide, N-chloroamines, chlorohydantoins such as dichlorodimethyl hydantoin and chlorobromo dimethylhydantoin, bromo-compounds corresponding to the chloro-compounds above.

The compositions of the present invention do not comprise a bleach activator. By "bleach activator", it is meant herein a compound which reacts with peroxygen bleach like hydrogen peroxide to form a peracid. The peracid thus formed constitutes the activated bleach. Bleach activators that are not to be used in the composition include, but are not limited to, those belonging to the class of esters, amides, imides, or anhydrides. Examples of bleach activators that are not to be used in the composition include, but are not limited to, TAED, sodium 3,5,5 trimethyl hexanoyloxy-benzene sulphonate, diperoxy dodecanoic acid, nonylamide of peroxyadipic acid, nonylamide of peroxyadipic acid, n-nonanoyloxybenzenesulphonate (NOBS), acetyl triethyl citrate (ATC), n-alkyl alkyl ammonium acetonitrile activators. Examples of bleach activators that are not to be used in the composition include, but are not limited to, are N-acyl caprolactams selected from the group consisting of substituted or unsubstituted benzoyl caprolactam, octanoyl caprolactam, nonanoyl caprolactam, hexanoyl caprolactam, decanoyl caprolactam, undecenoyl caprolactam, formyl caprolactam, acetyl caprolactam, propanoyl caprolactam, butanoyl caprolactam pentanoyl caprolactam or mixtures thereof.

Suitably, the calcium hypochlorite, magnesium hypochlorite and mixtures thereof in the first part of the solid-layered composition is present in the composition in an amount ranging from about 0.1% to about 50%, about 0.1% to about 45%, about 0.1% to about 40%, about 0.1% to about 30%, about 0.1% to about 25%, about 0.1% to about 20%, about 0.1% to about 15%, about 0.1% to about 10%, about 0.1% to about 5%, about 5% to about 20%, about 5% to about 15%, about 10% to about 20%, about 10% to about 15% and about 15% to about 20%.

Builders

The composition can contain a builder. In one embodiment, the first and second part of the solid-layered composition can contain a builder. In another embodiment, the first part of the solid-layered composition only contains a builder. In another embodiment, the second part of the solid-layered composition only contains a builder. Suitably, the builder is present in the cleaning composition in an amount ranging from about 10% to about 90%, about 20% to about 90%, about 20% to about 80%, about 20% to about 60%, about 20% to about 50%, about 30% to about 60%, about 35 to about 55%, about 40 to about 50%, about 20% to about 30% to 55%, about 30% to about 50%, about 30% to about 45%, about 30% to about 40%, about 20% to about 60%, about 25% to about 60%, about 20% to about 40%, about 20% to about 30%. The builder can be selected from inorganic builders, such as alkali metal carbonate, alkali metal bicarbonate, alkali metal hydroxide, alkali metal silicate and combinations thereof.

The composition can include a builder, which can increase the effectiveness of the surfactant. The builder can also function as a softener, a sequestering agent, a buffering agent, or a pH adjusting agent in the cleaning composition. A variety of builders or buffers can be used and they include, but are not limited to, phosphate-silicate compounds, zeolites, alkali metal, ammonium and substituted ammonium polyacetates, trialkali salts of nitrilotriacetic acid, carboxylates, polycarboxylates, carbonates, bicarbonates, polyphosphates, aminopolycarboxylates, polyhydroxy-sulfonates, and starch derivatives. Builders, when used, include, but are not limited to, organic acids, mineral acids, alkali metal and alkaline earth salts of silicate, metasilicate, polysilicate, borate, sulfates, hydroxide, carbonate, carbamate, phosphate, polyphosphate, pyrophosphates, triphosphates, tetraphosphates, ammonia, hydroxide, monoethanolamine, monopropanolamine, diethanolamine, dipropanolamine, triethanolamine, and 2-amino-2-methylpropanol. Other suitable buffers include ammonium carbamate, citric acid, and acetic acid. Mixtures of any of the above are also acceptable. Useful inorganic buffers/alkalinity sources include ammonia, the alkali metal carbonates and alkali metal phosphates, e.g., sodium carbonate, sodium polyphosphate. For additional buffers see WO 95/07971, which is incorporated herein by reference. Other preferred pH adjusting agents include sodium or potassium hydroxide. The term silicate is meant to encompass silicate, metasilicate, polysilicate, aluminosilicate and similar compounds. Preferred buffers for both first and second parts of the solid-layered composition include carbonate, bicarbonate, sesquicarbonate and mixtures thereof.

Water-Soluble Polymer

The composition can contain a water-soluble polymer. In one embodiment, the first part of the solid-layered composition can contain a water-soluble polymer. In another embodiment, the second part of the solid-layered composition can contain a water-soluble polymer. In another embodiment, the first and second parts of the solid-layered composition can contain a water-soluble polymer. Examples of water-soluble polymer include, but are not limited to, polycarboxylate, sulfonated carboxylate, polysulfonate, polyvinylpyrrolidone ("PVP"), and mixtures thereof.

Examples of polycarboxylate include, but are not limited to, polymers with sufficient carboxylate ions to achieve water solubility. Carboxylate ions may be derived from various monomers including acrylic acid, maleic acid and maleic anhydride. Copolymers of different carboxylate-containing monomers are also suitable as well as copolymers with non carboxylate containing monomers such as methacrylate, acrylonitrile, styrene, ethylene, propylene, and many others. Mixtures of carboxylate containing polymers can also be used.

Suitably, the molecular weight of the water-soluble polymer may be between about 1,000 to about 10,000 daltons, about 1,000 to about 8,000 daltons, about 1,000 to about 6,000 daltons, about 1,000 to about 5,000 daltons, about 1,000 to about 4,000 daltons, about 1,000 to about 2,000 daltons, about 2,000 to about 10,000 daltons, about 2,000 to about 8,000 daltons, about 2,000 to about 6,000 daltons, about 2,000 to about 5,000 daltons, about 2,000 to about 4,000 daltons, about 3,000 to about 10,000 daltons, about 3,000 to about 8,000 daltons, about 3,000 to about 6,000 daltons, about 3,000 to about 5,000 daltons, about 3,000 to about 5,000 daltons, about 4,000 to about 10,000 daltons, about 4,000 to about 8,000 daltons, about 4,000 to about 6,000 daltons, about 5,000 to about 10,000 daltons, about 5,000 to about 7,500 daltons, and about 7,500 to about 10,000 daltons.

Suitably, the water-soluble polymer is present in an amount ranging from about 0.1% to about 60%, about 0.1% to about 50%, about 0.1% to about 40%, about 0.1% to about 30%, about 0.1% to about 20%, about 0.1% to about 15%, about 0.1% to about 10%, about 5% to about 60%, about 5% to about 50%, about 5% to about 40%, about 5% to about 30%, about 5% to about 20%, about 5% to about 10%, about 10% to about 60%, about 10% to about 50%, about 10% to about 40%, about 10% to about 30%, about 10% to 20%, about 20% to about 60%, about 20% to about 50%, about 20% to about 40%, about 20% to about 30%, about 30% to about 60%, about 30% to about 50%, about 30% to about 40%, about 40% to about 60%.

Acid

The composition can contain an acid. In one embodiment, both parts of the solid-layered composition comprise an acid. In another embodiment, the first part of the solid-layered composition only comprises an acid. In another embodiment, the second part of the solid-layered composition only comprises an acid. Examples of acids that can be used with the present invention include, but are not limited to, sulfonic acid, dicarboxylic acid, monocarboxylic acid, aminocarboxylic acid and mixtures thereof. Specific examples of acids, include but are not limited to, succinic acid, glutaric acid, 3-pyridine sulfonic acid, dodecyl benzene sulfonic acid, and mixtures thereof.

The first part of the composition does not contain carboxylic acids that have one or more hydroxyl group moieties. Examples of acids that are not to be used in the composition include, but are not limited to, citric acid, tartaric acid. The first part of the composition also does not contain aliphatic or aromatic amines that possess a covalently bound proton to the nitrogen moiety. Examples of acids that are not to be used in the composition include, but are not limited to alanine.

Suitably, the acid is present in an amount ranging from about 0.1% to about 50%, about 0.1% to about 40%, about 0.1% to about 30%, about 0.1% to about 20%, about 0.1% to about 15%, about 0.1% to about 10%, about 5% to about 50%, about 5% to about 40%, about 5% to about 30%, about 5% to about 20%, about 5% to about 10%, about 10% to about 50%, about 10% to about 40%, about 10% to about 30%, about 10% to 20%, about 20% to about 50%, about 20% to about 40%, about 20% to about 30%, about 30% to about 50%, about 30% to about 40%, about 40% to about 50%.

Cross-Linked Water-Swellable Polymer

The composition may optionally contain a cross-linked water-swellable polymer. In one embodiment, the first part of the solid-layered composition only contains a cross-linked water-swellable polymer. In another embodiment, the second part of the solid-layered composition only contains a cross-linked water-swellable polymer. In another embodiment, the first and second parts of the solid-layered composition contain a cross-linked water-swellable polymer. Examples of water-swellable polymer include, but are not limited to, cross-linked polycarboxylate, cross-linked polysulfonate, cross-linked carboxymethylcellulose, cross-linked PVP, cross-linked carboxymethyl cellulose, cellulose, sodium carboxymethylcellulose and mixtures thereof.

Suitably, the molecular weight of the water-swellable polymer may be between about 1,000 to about 10,000 daltons, about 1,000 to about 8,000 daltons, about 1,000 to about 6,000 daltons, about 1,000 to about 5,000 daltons, about 1,000 to about 4,000 daltons, about 1,000 to about 2,000 daltons, about 2,000 to about 10,000 daltons, about 2,000 to about 8,000 daltons, about 2,000 to about 6,000 daltons, about 2,000 to about 5,000 daltons, about 2,000 to about 4,000 daltons, about 3,000 to about 10,000 daltons, about 3,000 to about 8,000 daltons, about 3,000 to about 6,000 daltons, about 3,000 to about 5,000 daltons, about 3,000 to about 5,000 daltons, about 4,000 to about 10,000 daltons, about 4,000 to about 8,000 daltons, about 4,000 to about 6,000 daltons, about 5,000 to about 10,000 daltons, about 5,000 to about 7,500 daltons, and about 7,500 to about 10,000 daltons.

Suitably, the water-swellable polymer is optionally present in an amount ranging from about 0.1% to about 60%, about 0.1% to about 50%, about 0.1% to about 40%, about 0.1% to about 30%, about 0.1% to about 20%, about 0.1% to about 15%, about 0.1% to about 10%, about 5% to about 60%, about 5% to about 50%, about 5% to about 40%, about 5% to about 30%, about 5% to about 20%, about 5% to about 10%, about 10% to about 60%, about 10% to about 50%, about 10% to about 40%, about 10% to about 30%, about 10% to 20%, about 20% to about 60%, about 20% to about 50%, about 20% to about 40%, about 20% to about 30%, about 30% to about 60%, about 30% to about 50%, about 30% to about 40%, about 40% to about 60%.

Surfactants

The composition may contain one or more surfactants selected from nonionic, anionic, cationic, ampholytic, amphoteric and zwitterionic surfactants and mixtures thereof. Preferably, the surfactant is present in the second part of the solid-layered composition. A typical listing of anionic, ampholytic, and zwitterionic classes, and species of these surfactants, is given in U.S. Pat. No. 3,929,678 to Laughlin and Heuring. A list of suitable cationic surfactants is given in U.S. Pat. No. 4,259,217 to Murphy. The surfactants may be present at a level of from about 0.1% to about 25%, or from about 0.1% to about 20%, or from about 0.1% to about 15%, or from about 0.1% to about 10%, or from about 0.1% to about 5%, or from about 5% to about 20%, or from about 5% to about 15%, or from about 5% to about 10%, or from about 10% to about 20%, or from about 10% to about 15%, or from about 15% to about 20%.

The composition may comprise an anionic surfactant. Essentially any anionic surfactants useful for detersive purposes can be used in the cleaning composition. These can include salts (including, for example, sodium, potassium, ammonium, and substituted ammonium salts such as mono-, di- and tri-ethanolamine salts) of the anionic sulfate, sulfonate, carboxylate and sarcosinate surfactants. Anionic surfactants may comprise a sulfonate or a sulfate surfactant. Anionic surfactants may comprise an alkyl sulfate, a linear or branched alkyl benzene sulfonate, or an alkyldiphenyloxide disulfonate, as described herein.

Other anionic surfactants include the isethionates such as the acyl isethionates, N-acyl taurates, fatty acid amides of methyl tauride, alkyl succinates and sulfosuccinates, monoesters of sulfosuccinate (for instance, saturated and unsaturated C12-C18 monoesters) diesters of sulfosuccinate (for instance saturated and unsaturated C6-C14 diesters), N-acyl sarcosinates. Resin acids and hydrogenated resin acids are also suitable, such as rosin, hydrogenated rosin, and resin acids and hydrogenated resin acids present in or derived from tallow oil. Anionic sulfate surfactants suitable for use herein include the linear and branched primary and secondary alkyl sulfates, alkyl ethoxysulfates, fatty oleoyl glycerol sulfates, alkyl phenol ethylene oxide ether sulfates, the C5-C17acyl-N—(C1-C4 alkyl) and —N—(C1-C2 hydroxyalkyl) glucamine sulfates, and sulfates of alkylpolysacchanides such as the sulfates of alkylpolyglucoside (the nonionic nonsulfated compounds being described herein). Alkyl sulfate surfactants may be selected from the linear and branched primary C10-C18 alkyl sulfates, the C11-C15 branched chain alkyl sulfates, or the C12-C14 linear chain alkyl sulfates.

Alkyl ethoxysulfate surfactants may be selected from the group consisting of the C10-C18 alkyl sulfates, which have been ethoxylated with from 0.5 to 20 moles of ethylene oxide per molecule. The alkyl ethoxysulfate surfactant may be a C11-C18, or a C11-C15 alkyl sulfate which has been ethoxylated with from 0.5 to 7, or from 1 to 5, moles of ethylene oxide per molecule. One aspect of the invention employs mixtures of the alkyl sulfate and/or sulfonate and alkyl ethoxysulfate surfactants. Such mixtures have been disclosed in PCT Patent Application No. WO 93/18124.

Anionic sulfonate surfactants suitable for use herein include the salts of C5-C20 linear alkylbenzene sulfonates, alkyl ester sulfonates, C6-C22 primary or secondary alkane sulfonates, C6-C24 olefin sulfonates, sulfonated polycarboxylic acids, alkyl glycerol sulfonates, fatty acyl glycerol sulfonates, fatty oleyl glycerol sulfonates, and any mixtures thereof. Suitable anionic carboxylate surfactants include the alkyl ethoxy carboxylates, the alkyl polyethoxy polycarboxylate surfactants and the soaps ('alkyl carboxyls'), especially certain secondary soaps as described herein. Suitable alkyl ethoxy carboxylates include those with the formula $$RO(CH_2CH_2O)_xCH_2COO^-M^+$$

wherein R is a C6 to C18 alkyl group, x ranges from 0 to 10, and the ethoxylate distribution is such that, on a weight basis, the amount of material where x is 0 is less than 20% and M is a cation. Suitable alkyl polyethoxypolycarboxylate surfactants include those having the formula RO—(CHR$^1$—CHR$^2$—O)—R$^3$ wherein R is a C6 to C18 alkyl group, x is from 1 to 25, R$^1$ and R$^2$ are selected from the group consisting of hydrogen, methyl acid radical, succinic acid radical, hydroxysuccinic acid radical, and mixtures thereof, and R$^3$ is selected from the group consisting of hydrogen, substituted or unsubstituted hydrocarbon having between 1 and 8 carbon atoms, and mixtures thereof.

Suitable soap surfactants include the secondary soap surfactants, which contain a carboxyl unit connected to a secondary carbon. Suitable secondary soap surfactants for use herein are water-soluble members selected from the group consisting of the water-soluble salts of 2-methyl-1-undecanoic acid, 2-ethyl-1-decanoic acid, 2-propyl-1-nonanoic acid, 2-butyl-1-octanoic acid and 2-pentyl-1-heptanoic acid. Certain soaps may also be included as suds suppressors.

Other suitable anionic surfactants are the alkali metal sarcosinates of formula R—CON(R$^1$) CH—)COOM, wherein R is a C5-C17 linear or branched alkyl or alkenyl group, R$^1$ is a C1-C4 alkyl group and M is an alkali metal ion. Examples are the myristyl and oleoyl methyl sarcosinates in the form of their sodium salts.

Other suitable surfactants include fatty acid sarosinates which are mild, biodegradable anionic surfactants derived from fatty acids and sarcosine (amino acid). Sarcosine is the N-methyl derivative of glycine. Sarcosine is a natural amino acid found in muscles and other tissues. Sarcosine is found naturally as an intermediate in the metabolism of choline to glycine. In a preferred embodiment, the sarcosines are acyl sarcosines. Examples of acyl sarcosines include, but are not limited to, cocoyl sarcosine, lauroyl sarcosine, myristoyl sarcosine, oleoyl sarcosine, stearoyl sarcosine which are modified fatty acids. The salts of acyl sarcosines are referred to acyl sarcosinates. Acyl sarcosinates useful herein include, for example, those having a formula:

$$RCON(CH_3)CH2COOX$$

wherein R is an alkyl or alkenyl having from 8 to 22 carbon atoms, preferably from 12 to 18 carbon atoms, more preferably from 12 to 14 carbon atoms; and X is a sodium, potassium, ammonium, or triethanolamine.

Examples of acyl sarcosinates that can be used with the present invention include, but not limited to, sodium coccyl sarcosinate, sodium lauroyl sarcosinate and sodium myristoyl sarcosinate, sodium oleoyl sarcosinate, sodium stearoyl sarcosinate, ammonium coccyl sarcosinate, ammonium lauroyl sarcosinate and ammonium myristoyl sarcosinate, ammonium oleoyl sarcosinate and ammonium stearoyl sarcosinate. Commercially available preferred acyl sarcosinates include, but are not limited to, for example, sodium lauroyl sarcosinate having the tradename Hamposyl® L30 which is available from Hampshire Chemicals, and sodium cocoyl sarcosinate having the tradename Hamposyl® C30 which is available from Hampshire Chemicals.

Other suitable surfactants include fatty alcohol sulfate which has a higher alcohol or alkyl group is normally in the range of 10 to 18 carbon atoms. The cation will almost invariably be sodium or will include sodium, although other cations, such as triethanolamine, potassium, ammonium, magnesium and calcium. Preferred fatty alcohol sulfates are those wherein the fatty alcohol is essentially saturated and is of carbon content(s) within the 10 to 18 carbon atoms range, preferably 10 or 12 to 14 or 16 carbon atoms, such as 12 to 16, or that is derived from coconut oil (coco), palm oil, or palm kernel oil. Lauryl sulfates, and particularly, sodium lauryl sulfate, are preferred primary detergents but such designation also may apply to such detergents wherein the carbon chain length of the alcohol is not limited to 12 carbon atoms, but is primarily (over 50% and normally over 70 or 75%) of 12 to 14 carbon atoms. Such materials may be obtained from natural sources, such as coconut oil and palm kernel oil. In one embodiment, the fatty alcohol sulfate is a C12-C18 fatty alcohol sulfate. In another embodiment, the fatty alcohol sulfate is a C12-C16 fatty alcohol sulfate. In another embodiment, the fatty alcohol sulfate is a C12-C14 fatty alcohol sulfate. In another embodiment, the fatty alcohol is a C12 fatty alcohol sulfate. In another embodiment, the fatty alcohol sulfate is sodium lauryl sulfate. In a specific embodiment, the fatty alcohol sulfate is a sodium coco fatty alcohol sulfate.

Suitable amphoteric surfactants for use herein include the amine oxide surfactants and the alkyl amphocarboxylic acids. Suitable amine oxides include those compounds having the formula $R^3(OR^4)_xNO(R^5)_2$ wherein $R^3$ is selected from an alkyl, hydroxyalkyl, acylamidopropyl and alkylphenyl group, or mixtures thereof, containing from 8 to 26 carbon atoms; $R^4$ is an alkylene or hydroxyalkylene group containing from 2 to 3 carbon atoms, or mixtures thereof, x is from 0 to 5, preferably from 0 to 3; and each $R^5$ is an alkyl or hydroxyalkyl group containing from 1 to 3, or a polyethylene oxide group containing from 1 to 3 ethylene oxide groups. Suitable amine oxides are C10-C18 alkyl dimethylamine oxide, and C10-18 acylamido alkyl dimethylamine oxide. A suitable example of an alkyl amphodicarboxylic acid is Miranol™ C2M Conc. manufactured by Miranol, Inc., Dayton, N.J.

Zwitterionic surfactants can also be incorporated into the cleaning compositions. These surfactants can be broadly described as derivatives of secondary and tertiary amines, derivatives of heterocyclic secondary and tertiary amines, or derivatives of quaternary ammonium, quaternary phosphoniurn or tertiary sulfonium compounds. Betaine and sultaine surfactants are exemplary zwittenionic surfactants for use herein.

Suitable betaines are those compounds having the formula $R(R^1)_2N^+R^2COO^-$ wherein R is a C6-C18 hydrocarbyl group, each $R^1$ is typically C1-C3 alkyl, and $R^2$ is a C1-C5 hydrocarbyl group. Suitable betaines are C12-18 dimethylammonio hexanoate and the C10-18 acylamidopropane (or ethane) dimethyl (or diethyl) betaines. Complex betaine surfactants are also suitable for use herein.

Suitable cationic surfactants to be used herein include the quaternary ammonium surfactants. The quaternary ammonium surfactant may be a mono C6-C16, or a C6-C 10 N-alkyl or alkenyl ammonium surfactant wherein the remaining N positions are substituted by methyl, hydroxyethyl or hydroxypropyl groups. Suitable are also the mono-alkoxylated and bis-alkoxylated amine surfactants. Additional suitable cationic surfactants include coco fatty acid diethanolamine, hydrogenated palm tea ester quat, and cationic ethyoxylate fatty acids.

Another suitable group of cationic surfactants, which can be used in the cleaning compositions, are cationic ester surfactants. The cationic ester surfactant is a compound having surfactant properties comprising at least one ester (i.e. —COO—) linkage and at least one cationically charged group. Suitable cationic ester surfactants, including choline ester surfactants, have for example been disclosed in U.S. Pat. Nos. 4,228,042, 4,239,660 and 4,260,529. The ester linkage and cationically charged group may be separated from each other in the surfactant molecule by a spacer group consisting of a chain comprising at least three atoms (i.e. of three atoms chain length), or from three to eight atoms, or from three to five atoms, or three atoms. The atoms forming the spacer group chain are selected from the group consisting, of carbon, nitrogen and oxygen atoms and any mixtures thereof, with the proviso that any nitrogen or oxygen atom in said chain connects only with carbon atoms in the chain. Thus spacer groups having, for example, —O—O— (i.e. peroxide), —N—N—, and —N—O— linkages are excluded, whilst spacer groups having, for example $—CH_2—O—$, $CH_2—$ and $—CH_2—NH—CH_2—$ linkages are included. The spacer group chain may comprise only carbon atoms, or the chain is a hydrocarbyl chain.

The cleaning composition may comprise cationic monoalkoxylated amine surfactants, for instance, of the general formula: $R^1R^2R^3N^+ApR^4X^-$ wherein $R^1$ is an alkyl or alkenyl moiety containing from about 6 to about 18 carbon atoms, or from 6 to about 16 carbon atoms, or from about 6 to about 14 carbon atoms; $R^2$ and $R^3$ are each independently alkyl groups containing from one to about three carbon atoms, for instance, methyl, for instance, both $R^2$ and $R^3$ are methyl groups; $R^4$ is selected from hydrogen, methyl and ethyl; $X^-$ is an anion such as chloride, bromide, methylsulfate, sulfate, or the like, to provide electrical neutrality; A is a alkoxy group, especially a ethoxy, propoxy or butoxy group; and p is from 0 to about 30, or from 2 to about 15, or from 2 to about 8. The $ApR^4$ group in the formula may have p=1 and is a hydroxyalkyl group, having no greater than 6 carbon atoms whereby the —OH group is separated from the quaternary ammonium nitrogen atom by no more than 3 carbon atoms. Suitable $ApR^4$ groups are $—CH_2CH_2—OH$, $—CH_2CH_2CH_2—OH$, $—CH_2CH(CH_3)—OH$ and $—CH(CH_3)CH_2—OH$. Suitable $R^1$ groups are linear alkyl groups, for instance, linear $R^1$ groups having from 8 to 14 carbon atoms.

Suitable cationic mono-alkoxylated amine surfactants for use herein are of the formula $R^1(CH_3)(CH_3)N^+(CH_2CH_2O)_{2-5}H\ X^-$ wherein $R^1$ is C10-C18 hydrocarbyl and mixtures thereof, especially C10-C14 alkyl, or C10 and C12 alkyl, and X is any convenient anion to provide charge balance, for instance, chloride or bromide.

As noted, compounds of the foregoing type include those wherein the ethoxy ($CH_2CH_2O$) units (EO) are replaced by butoxy, isopropoxy [$CH(CH_3)CH_2O$] and [$CH_2CH(CH_3)O$] units (i-Pr) or n-propoxy units (Pr), or mixtures of EO and/or Pr and/or i-Pr units.

The cationic bis-alkoxylated amine surfactant may have the general formula: $R^1R^2N^+ApR^3A'qR^4X^-$ wherein $R^1$ is an alkyl or alkenyl moiety containing from about 8 to about 18 carbon atoms, or from 10 to about 16 carbon atoms, or from about 10 to about 14 carbon atoms; $R^2$ is an alkyl group containing from one to three carbon atoms, for instance, methyl; $R^3$ and $R^4$ can vary independently and are selected from hydrogen, methyl and ethyl, $X^-$ is an anion such as chloride, bromide, methylsulfate, sulfate, or the like, sufficient to provide electrical neutrality. A and A' can vary independently and are each selected from C1-C4 alkoxy, for instance, ethoxy, (i.e., $—CH_2CH_2O—$), propoxy, butoxy and mixtures thereof, p is from 1 to about 30, or from 1 to about 4 and q is from 1 to about 30, or from 1 to about 4, or both p and q are 1.

Suitable cationic bis-alkoxylated amine surfactants for use herein are of the formula $R^1CH_3N^+(CH_2CH_2OH)(CH_2CH_2OH)\ X^-$, wherein $R^1$ is C10-C18 hydrocarbyl and mixtures thereof, or C10, C12, C14 alkyl and mixtures thereof, $X^-$ is any convenient anion to provide charge balance, for example, chloride. With reference to the general cationic bis-alkoxylated amine structure noted above, since in one example compound $R^1$ is derived from (coconut) C12-C14 alkyl fraction fatty acids, $R^2$ is methyl and $ApR^3$ and $A'qR^4$ are each monoethoxy.

Other cationic bis-alkoxylated amine surfactants useful herein include compounds of the formula: $R^1R^2N^+—(CH_2CH_2O)_pH—(CH_2CH_2O)_qH\ X^-$ wherein $R^1$ is C10-C18 hydrocarbyl, or C10-C14 alkyl, independently p is 1 to about 3 and q is 1 to about 3, $R^2$ is C1-C3 alkyl, for example, methyl, and $X^-$ is an anion, for example, chloride or bromide.

Other compounds of the foregoing type include those wherein the ethoxy ($CH_2CH_2O$) units (EO) are replaced by butoxy (Bu) isopropoxy [$CH(CH_3)CH_2O$] and [$CH_2CH(CH_3)O$] units (i-Pr) or n-propoxy units (Pr), or mixtures of EO and/or Pr and/or i-Pr units.

The inventive compositions may include at least one fluorosurfactant selected from nonionic fluorosurfactants, cationic fluorosurfactants, and mixtures thereof which are soluble or dispersible in the aqueous compositions being taught herein, sometimes compositions which do not include further detersive surfactants, or further organic solvents, or both. Suitable nonionic fluorosurfactant compounds are found among the materials presently commercially marketed under the tradename Fluorad® (ex. 3M Corp.) Exemplary fluorosurfactants include those sold as Fluorad® FC-740, generally described to be fluorinated alkyl esters; Fluorad® FC-430, generally described to be fluorinated alkyl esters; Fluorad® FC-431, generally described to be fluorinated alkyl esters; and, Fluorad® FC-170-C, which is generally described as being fluorinated alkyl polyoxyethlene ethanols.

An example of a suitable cationic fluorosurfactant compound has the following structure: $C_nF_{2n+1}SO_2NHC_3H_6N^+(CH_3)_3I^-$ where n~8. This cationic fluorosurfactant is available under the tradename Fluorad® FC-135 from 3M. Another example of a suitable cationic fluorosurfactant is $F_3$ $$—(CF_2)_n—(CH_2)_mSCH_2CHOH—CH_2—N^+R_1R_2R_3Cl^-$$

wherein: n is 5-9 and m is 2, and $R_1$, $R_2$ and $R_3$ are $—CH_3$. This cationic fluorosurfactant is available under the tradename ZONYL® FSD (available from DuPont, described as 2-hydroxy-3-((gamma-omega-perfluoro-$C_{6-20}$-alkyl)thio)-N,N,N-trimethyl-1-propyl ammonium chloride). Other cationic fluorosurfactants suitable for use in the present invention are also described in EP 866,115 to Leach and Niwata. The fluorosurfactant selected from the group of nonionic fluorosurfactant, cationic fluorosurfactant, and mixtures thereof may be present in amounts of from 0.001 to 5% wt., preferably from 0.01 to 1% wt., and more preferably from 0.01 to 0.5% wt.

The composition may comprise a nonionic surfactant. Essentially any alkoxylated nonionic surfactants are suitable herein, for instance, ethoxylated and propoxylated nonionic surfactants. Alkoxylated surfactants can be selected from the classes of the nonionic condensates of alkyl phenols, nonionic ethoxylated alcohols, nonionic ethoxylated/propoxylated fatty alcohols, nonionic ethoxylate/propoxylate condensates with propylene glycol, and the nonionic ethoxylate condensation products with propylene oxide/ethylene diamine adducts.

The condensation products of aliphatic alcohols with from 1 to 25 moles of alkylene oxide, particularly ethylene oxide and/or propylene oxide, are suitable for use herein. The alkyl chain of the aliphatic alcohol can either be straight or branched, primary or secondary, and generally contains from 6 to 22 carbon atoms. Also suitable are the condensation products of alcohols having an alkyl group containing from 8 to 20 carbon atoms with from 2 to 10 moles of ethylene oxide per mole of alcohol.

Polyhydroxy fatty acid amides suitable for use herein are those having the structural formula $R^2CONR^1Z$ wherein: $R^1$ is H, C1-C4 hydrocarbyl, 2-hydroxyethyl, 2-hydroxypropyl, ethoxy, propoxy, or a mixture thereof, for instance, C1-C4 alkyl, or C1 or C2 alkyl; and $R^2$ is a C5-C31 hydrocarbyl, for instance, straight-chain C5-C19 alkyl or alkenyl, or straight-chain C9-C17 alkyl or alkenyl, or straight-chain C11-C17 alkyl or alkenyl, or mixture thereof-, and Z is a polyhydroxyhydrocarbyl having a linear hydrocarbyl chain with at least 3 hydroxyls directly connected to the chain, or an alkoxylated derivative (for example, ethoxylated or propoxylated) thereof. Z may be derived from a reducing sugar in a reductive amination reaction, for example, Z is a_glycityl.

Suitable fatty acid amide surfactants include those having the formula: $R^1CON(R^2)_2$ wherein $R^1$ is an alkyl group containing from 7 to 21, or from 9 to 17 carbon atoms and each $R^2$ is selected from the group consisting of hydrogen, C1-C4 alkyl, C1-C4 hydroxyalkyl, and $—(C_2H_4O)_xH$, where x is in the range of from 1 to 3.

Suitable alkylpolysaccharides for use herein are disclosed in U.S. Pat. No. 4,565,647 to Llenado, having a hydrophobic group containing from 6 to 30 carbon atoms and a polysaccharide, e.g., a polyglycoside, hydrophilic group containing from 1.3 to 10 saccharide units. Alkylpolyglycosides may have the formula: $R^2O(C_nH_{2n}O)_t(glycosyl)_x$ wherein $R^2$ is selected from the group consisting of alkyl, alkylphenyl, hydroxyalkyl, hydroxyalkylphenyl, and mixtures thereof in which the alkyl groups contain from 10 to 18 carbon atoms; n is 2 or 3; t is from 0 to 10, and x is from 1.3 to 8. The glycosyl may be derived from glucose.

Other suitable nonionic surfactants are food safe nonionic surfactants. Examples of food safe nonionic surfactants are sucrose esters, such as sucrose cocoate available from Croda, and sorbitan esters, such as polyoxyethylene(20) sorbitan monooleate from J.T. Baker and polyoxyethylene(20) sorbitan monolaurate from Uniquema. Other examples of food safe nonionic surfactants are given in Generally Recognized As Safe (GRAS) lists, as described below.

In a preferred embodiment, the compositions may specifically contain alkyl polyglucoside ("APG") surfactant. Suitable alkyl polyglucoside surfactants are the alkylpolysaccharides that are disclosed in U.S. Pat. No. 5,776,872 to Giret et al.; U.S. Pat. No. 5,883,059 to Furman et al.; U.S. Pat. No. 5,883,062 to Addison et al.; and U.S. Pat. No. 5,906,973 to Ouzounis et al., which are all incorporated by reference. Suitable alkyl polyglucosides for use herein are also disclosed in U.S. Pat. No. 4,565,647 to Llenado describing alkylpolyglucosides having a hydrophobic group containing from about 6 to about 30 carbon atoms, or from about 10 to about 16 carbon atoms and polysaccharide, e.g., a polyglycoside, hydrophilic group containing from about 1.3 to about 10, or from about 1.3 to about 3, or from about 1.3 to about 2.7 saccharide units. Optionally, there can be a polyalkyleneoxide chain joining the hydrophobic moiety and the polysaccharide moiety. A suitable alkyleneoxide is ethylene oxide. Typical hydrophobic groups include alkyl groups, either saturated or unsaturated, branched or unbranched containing from about 8 to about 18, or from about 10 to about 16, carbon atoms. Suitably, the alkyl group can contain up to about 3 hydroxy groups and/or the polyalkyleneoxide chain can contain up to about 10, or less than about 5, alkyleneoxide moieties. Suitable alkyl polysaccharides are octyl, nonyldecyl, undecyldodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses and/or galactoses. Suitable mixtures include coconut alkyl, di-, tri-, tetra-, and pentaglucosides and tallow alkyl tetra-, penta-, and hexaglucosides.

Suitable alkylpolyglycosides (or alkylpolyglucosides) have the formula: $R^2O(C_nH_{2n}O)_t(glucosyl)_x$ wherein $R^2$ is selected from the group consisting of alkyl, alkylphenyl, hydroxyalkyl, hydroxyalkylphenyl, and mixtures thereof in which the alkyl groups contain from about 10 to about 18, preferably from about 12 to about 14, carbon atoms; n is about 2 or about 3, preferably about 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

A group of alkyl glycoside surfactants suitable for use in the practice of this invention may be represented by formula I below:

$$RO—(R^2O)_y-(G)_xZ_b \quad I$$

wherein R is a monovalent organic radical containing from about 6 to about 30 (preferably from about 8 to about 18) carbon atoms; $R^2$ is a divalent hydrocarbon radical containing from about 2 to about 4 carbon atoms; 0 is an oxygen atom; y is a number which has an average value from about 0 to about 1 and is preferably 0; G is a moiety derived from a reducing saccharide containing 5 or 6 carbon atoms; and x is a number having an average value from about 1 to 5 (preferably from 1.1 to 2); Z is $O_2M^1$, $O_2CR^3$, $O(CH_2)$, $CO_2M^1$, $OSO_3M^1$, or $O(CH_2)SO_3M^1$; $R^3$ is $(CH_2)CO_2M^1$ or $CH{=}CHCO_2M^1$; (with the proviso that Z can be $O_2M^1$ only if Z is in place of a primary hydroxyl group in which the primary hydroxyl-bearing carbon atom, $—CH_2OH$, is oxidized to form a $—CO_2M^1$ group); b is a number from 0 to 3x+1 preferably an average of from 0.5 to 2 per glycosal group; p is 1 to 10, $M^1$ is $H^+$ or an organic or inorganic cation, such as, for example, an alkali metal, ammonium, monoethanolamine, or calcium. As defined in Formula I, R is generally the residue of a fatty alcohol having from about 8 to 30 or 8 to 18 carbon atoms. Suitable alkylglycosides include, for example, APG 325® (a $C_9$-$C_{11}$ alkyl polyglycoside available from Cognis Corporation), APG 625® (a $C_{10}$-$C_{16}$ alkyl polyglycoside available from Cognis Corporation), Dow Triton® CG110 (a $C_8$-$C_{10}$ alkyl polyglycoside available from Dow Chemical Company), AG6202® (a $C_8$ alkyl polyglycoside available from Akzo Nobel) Glucopon® 425N (a $C_8$-$C_{16}$ alkyl polyglycoside available from Cognis Corporation), Glucopon® 215 (a $C_8$-$C_{10}$ alkyl polyglycoside available from Cognis Corporation), Glucpon® 225 (a $C_8$-$C_{10}$ alkyl polyglycoside available from Cognis Corporation) and Alkadet 15® (a $C_8$-$C_{10}$ alkyl polyglycoside available from Huntsman Corporation). A C8 to C10 alkylpoly-glucoside includes alkylpoly-glucosides wherein the alkyl group is substantially C8 alkyl, substantially C10 alkyl, or a mixture of substantially C8 and C10 alkyl. Additionally, short chain APGs such as C4 and/or C6 or mixtures thereof will be suitable with the present invention.

Additional Adjuncts

The compositions optionally contain one or more of the following adjuncts: stain and soil repellants, lubricants, odor control agents, perfumes, fragrances and fragrance release agents, fillers, desiccants, dye, thickeners, colorants, enzymes, brighteners, and fluorescent whitening agents. Other adjuncts include, but are not limited to, acids, electrolytes, dyes and/or colorants, solubilizing materials, stabilizers, thickeners, anti-corrosion-inhibitors, defoamers, hydrotropes, cloud point modifiers, solid processing aids, binders, preservatives, and other polymers. Binders, when used, include, but are not limited to, celluloses, starches, gums, and synthetic polymers. The solubilizing materials, when used, include, but are not limited to, hydrotropes (e.g. water soluble salts of low molecular weight organic acids such as the sodium and/or potassium salts of toluene, cumene, and xylene sulfonic acid). Solid processing aids, when used, include, but are not limited to, flow aids, lubricants, anti-static agents, and glidants. Electrolytes, when used, include, calcium, sodium and potassium chloride. Thickeners, when used, include, but are not limited to, xanthan gum, calcium carbonate, cellulose, aluminum oxide, alginates, guar gum, methyl, ethyl, clays, and/or propyl hydroxycelluloses. Defoamers, when used, include, but are not limited to, silicones, aminosilicones, silicone blends, and/or silicone/hydrocarbon blends.

Preservatives, when used, include, but are not limited to, mildewstat or bacteriostat, methyl, ethyl and propyl parabens, phosphates such as trisodium phosphate, short chain organic acids (e.g. acetic, lactic and/or glycolic acids), bisguanidine compounds (e.g. Dantagard and/or Glydant) and/or short chain alcohols (e.g. ethanol and/or IPA). The mildewstat or bacteriostat includes, but is not limited to, mildewstats (including non-isothiazolone compounds) including Kathon GC, a 5-chloro-2-methyl-4-isothiazolin-3-one, KATHON ICP, a 2-methyl-4-isothiazolin-3-one, and a blend thereof, and KATHON 886, a 5-chloro-2-methyl-4-isothiazolin-3-one, all available from Rohm and Haas Company; BRONOPOL, a 2-bromo-2-nitropropane 1,3 diol, from Boots Company Ltd., PROXEL CRL, a propyl-p-hydroxybenzoate, from ICI PLC; NIPASOL M, an o-phenyl-phenol, $Na^+$ salt, from Nipa Laboratories Ltd., DOWICIDE A, a 1,2-Benzoisothiazolin-3-one, from Dow Chemical Co., Nipacides from Clariant, and IRGASAN DP 200, a 2,4,4'-trichloro-2-hydroxydiphenylether, from Ciba-Geigy A.G.

Third Part

The compositions of the present invention optionally may include a third part. In one embodiment, the third part is situated between the first and second part of the solid-layered composition. The third part may include, but not limited to, the following compounds, binder, filler, colorant, desiccant, solid processing aids, sodium chloride, sodium silicate, sodium sulfate, magnesium oxide, magnesium sulfate, magnesium carbonate, magnesium hydroxide, calcium carbonate, calcium hydroxide, calcium oxide, magnesium oxide, magnesium hydroxide, sodium carbonate, potassium carbonate, sodium bicarbonate, sodium sesquicarbonate, potassium sesquicarbonate, sodium borate, boric acid, aluminum hydroxide, silica, and mixtures thereof.

Form and Uses

The compositions of the present invention may used in the following non-limiting examples: hard surface cleaner, toilet bowl cleaner, laundry detergent, dishwashing detergent. The composition of the present invention may be in the form of a powder, tablet or a granule. The present invention is directed to composition claims and method of using the composition claims. The present invention may be used on hard surfaces or soft surfaces (i.e. fabric). Generally, methods steps of using the composition include, a) providing a specific surface b) contacting the surface with the claimed composition and c) cleaning the surface with the composition.

EXAMPLES

The compositions described below are sample solid-layered compositions that comprise at least two parts. The compositions are useful in cleaning, sanitizing or disinfecting soft or hard surfaces.

Example I illustrates a sample three-part solid-layered composition of the invention.

Example I

| First part | % wt. of first part |
|---|---|
| Calcium hypochlorite | 12.1% |
| Sodium carbonate | 34.5% |

-continued

| | |
|---|---|
| Succinic acid | 32.8% |
| Magnesium sulfate | 17.2% |
| Sodium polyacrylate (MW-5,400 daltons) | 3.4% |
| | % wt. of second part |
| Second part | |
| Sodium carbonate | 46.9% |
| Succinic acid | 44.6 |
| Sodium polyacrylate (MW-5,100 daltons) | 8.1% |
| Sodium linear alkylbenzene sulfonate | 0.4% |
| Third part | |
| Sodium chloride | 100% |

Example 2 illustrates a sample three-part solid-layered composition of the invention.

Example 2

| First part | % wt. of first part |
|---|---|
| Calcium hypochlorite | 42.3% |
| Sodium carbonate | 29.0% |
| Succinic acid | 27.6% |
| Sodium polyacrylate (MW-5,400 daltons) | 1.1% |
| **Second part** | **% wt. of second part** |
| Sodium carbonate | 60.3% |
| Succinic acid | 34.5% |
| PVP, crosslinked | 5.2% |
| **Third part** | **% wt. of third part** |
| Sodium carbonate | 100% |

Example 3 illustrates a sample three-part solid-layered composition of the invention.

Example 3

| First part | % wt. of first part |
|---|---|
| Calcium hypochlorite | 15.3% |
| Sodium carbonate | 53.4% |
| Succinic acid | 30.5% |
| PVP, crosslinked | 0.8% |
| **Second part** | **% wt. of second part** |
| Succinic acid | 35.9% |
| Sodium bicarbonate | 53.9% |
| Sodium polyacrylate (MW-4,500 daltons) | 9.3% |
| Sodium linear alkylbenzene sulfonate | 0.9% |
| **Third part** | **% wt. of third part** |
| Magnesium oxide | 100% |

Example 4 illustrates a sample three-part solid-layered composition of the invention.

Example 4

| First part | % wt. of first part |
|---|---|
| Calcium hypochlorite | 8.2% |
| Sodium carbonate | 45.9% |
| Succinic acid | 37.7% |
| Sodium polyacrylate maleic copolymer (MW-2,800 daltons) | 8.2% |
| **Second part** | **% wt. of second part** |
| Sodium polyacrylate (MW-5,100 daltons) | 6.1% |
| Sodium linear alkylbenzene sulfonate | 1.4% |
| PVP, crosslinked | 0.1% |
| Glutaric acid | 8.3% |
| Potassium bicarbonate | 84.1% |
| **Third part** | **% wt. of third part** |
| Magnesium sulfate | 100% |

Example 5 illustrates a sample two-part solid-layered composition of the invention.

Example 5

| First part | % wt. of first part |
|---|---|
| Calcium hypochlorite | 8.2% |
| Sodium carbonate | 45.9% |
| Succinic acid | 37.7% |
| Polycarboxylic maleic copolymer (MW-4,500 daltons) | 8.2% |
| **Second part** | **% wt. of second part** |
| Sodium polyacrylate (MW-5,100 daltons) | 9.7% |
| Sodium linear alkylbenzene sulfonate | 2.4% |
| PVP, crosslinked | 0.1% |
| Glutaric acid | 36.2% |
| Sodium sesquicarbonate | 51.6% |

Example 6 illustrates a sample three-part solid-layered composition of the invention.

Example 6

| First part | % wt. of first part |
|---|---|
| Calcium hypochlorite | 8.2% |
| Sodium carbonate | 45.9% |
| 3-Pyridine sulfonic acid | 37.7% |
| Polycarboxylic Maleic Copolymer (MW-4,500 daltons) | 8.2% |

-continued

| Second part | % wt. of second part |
|---|---|
| Sodium polyacrylate (MW-4,500 daltons) | 11.1% |
| Sodium bicarbonate | 49.9% |
| Sodium linear alkylbenzene sulfonate | 1.8% |
| Glutaric acid | 37.0% |
| Fragrance | 0.2% |
| **Third part** | **% wt. of third part** |
| Sodium sulfate | 100% |

Example 7 illustrates a sample three-part solid-layered composition of the invention.

Example 7

| First part | % wt. of first part |
|---|---|
| Calcium hypochlorite | 8.2% |
| Sodium carbonate | 45.9% |
| 3-Pyridine sulfonic acid | 37.7% |
| Polycarboxylic maleic copolymer (MW-4,500 daltons) | 4.1% |
| Laponite | 4.1% |
| **Second part** | **% wt. of second part** |
| Sodium carbonate | 41.7% |
| Succinic acid | 39.7% |
| Sodium polyacrylate (MW-5,100 daltons) | 1.0% |
| Magnesium sulfate | 17.6% |
| **Third part** | **% wt. of third part** |
| Magnesium hydroxide | 100% |

Example 8 illustrates a sample two-part solid-layered composition of the invention.

Example 8

| First part | % wt. of first part |
|---|---|
| Calcium hypochlorite | 8.2% |
| Sodium carbonate | 45.9% |
| 3-Pyridine sulfonic acid | 37.7% |
| Laponite | 4.1% |
| Sodium carboxymethylcellulose | 4.1% |
| **Second part** | **% wt. of second part** |
| Sodium carbonate | 40.8% |
| Succinic acid | 38.8% |
| Sodium polyacrylate (MW-5,100 daltons) | 1.0% |
| Sodium lauryl sulfate | 1.4% |
| Magnesium sulfate | 17.8% |
| Fragrance | 0.2% |

Example 9 illustrates a sample two-part solid-layered composition of the invention.

Example 9

| First part | % wt. of first part |
|---|---|
| Calcium hypochlorite | 8.2% |
| Sodium carbonate | 45.9% |
| Succinic acid | 37.7% |
| Sodium polyacrylate (MW-2,800 daltons) | 4.1% |
| Sodium carboxymethylcellulose | 4.1% |
| **Second part** | **% wt. of second part** |
| Sodium bicarbonate | 51.4% |
| Succinic acid | 42.2% |
| Sodium polyacrylate | 4.6% |
| Cross-linked Sodium carboxymethylcellulose | 0.9% |
| Laponite RD | 0.9% |

Example 10 illustrates a sample two-part solid-layered composition of the invention.

Example 10

| First part | % wt. of first part |
|---|---|
| Calcium hypochlorite | 8.2% |
| Sodium carbonate | 45.9% |
| Succinic acid | 37.7% |
| Sodium polyacrylate (MW-2,800 daltons) | 4.1% |
| Sodium xylene sulfonate | 4.1% |
| **Second part** | **% wt. of second part** |
| Sodium bicarbonate | 47.2% |
| Blue Dye | 0.01% |
| Succinic acid | 38.6 |
| Sodium polyacrylate (MW-2,800 daltons) | 4.2% |
| Hydroxypropyl cellulose | 0.8% |
| Laponite RD | 0.8% |
| Fragrance | 0.1% |
| Cross-linked sodium carboxymethylcellulose | 4.2% |
| Dodecyl benzene sulfonic acid | 0.58% |
| Sodium sulfate | 3.51% |

Example 11 illustrates a sample two-part solid-layered composition of the invention.

Example 11

| First part | % wt. of first part |
|---|---|
| Calcium hypochlorite | 8.2% |
| Sodium carbonate | 45.9% |
| Succinic acid | 37.7% |
| Sodium polyacrylate (MW-2,800 daltons) | 4.1% |
| Microcrystalline cellulose | 4.1% |

-continued

| Second part | % wt. of second part |
|---|---|
| Sodium bicarbonate | 54.5% |
| Succinic acid | 44.4% |
| Sodium xylene sulfonate | 1% |
| Sodium sulfate | 0.1% |

Example 12 illustrates a sample two-part solid-layered composition of the invention.

Example 12

| First part | % wt. of first part |
|---|---|
| Calcium hypochlorite | 8.2% |
| Sodium carbonate | 45.9% |
| Succinic acid | 37.7% |
| Sodium polyacrylate (MW-5,100 daltons) | 4.1% |
| Microcrystalline cellulose | 4.1% |
| **Second part** | **% wt. of second part** |
| Sodium bicarbonate | 51.5% |
| Succinic acid | 42.0% |
| Sodium xylene sulfonate | 1.0% |
| Sodium lauryl sulfate | 5.0% |
| Sodium sulfate | 0.5% |

Example 13 illustrates a sample two-part solid-layered composition of the invention.

Example 13

| First part | % wt. of first part |
|---|---|
| Calcium hypochlorite | 8.2% |
| Sodium carbonate | 45.9% |
| Sodium sulfate | 34.8% |
| Polyacrylic Acid (MW-2,600 daltons) | 2.9% |
| Microcrystalline cellulose | 4.1% |
| Sodium polyacrylate (MW-2,800 daltons) | 4.1% |
| **Second part** | **% wt. of second part** |
| Sodium bicarbonate | 53.47% |
| Succinic acid | 44.93% |
| Sodium lauryl sulfate | 0.97% |
| Styrene and acrylic acid terpolymer (MW-3,000 daltons) | 0.63% |

Example 14 illustrates a sample two-part solid-layered composition of the invention.

Example 14

| First part | % wt. of first part |
|---|---|
| Calcium hypochlorite | 8.2% |
| Sodium carbonate | 45.9% |
| Sodium sulfate | 23.6% |
| Dodecyl benzene sulfonic acid | 14.1% |
| Microcrystalline cellulose | 4.1% |
| Sodium polyacrylate (MW-2,800 daltons) | 4.1% |
| **Second part** | **% wt. of second part** |
| Sodium bicarbonate | 52.12% |
| Succinic acid | 44.93% |
| Linear 10-carbon hydrophobe Alkyldiphenyloxide Disulfonate | 2.33% |
| Styrene and acrylic acid terpolymer (MW-3,000 daltons) | 0.62% |

Example 15 illustrates a sample two-part solid-layered composition of the invention.

Example 15

| First part | % wt. of first part |
|---|---|
| Calcium hypochlorite | 8.2% |
| Sodium carbonate | 35.9% |
| Succinic acid | 47.7% |
| Sodium polyacrylate (MW-5,100 daltons) | 4.1% |
| Microcrystalline cellulose | 4.1% |
| **Second part** | **% wt. of second part** |
| Sodium bicarbonate | 52.12% |
| Succinic acid | 44.93% |
| Dowfax 2A1 Branched 12-carbon hydrophobe Alkyldiphenyloxide Disulfonate | 2.33% |
| Styrene and acrylic acid terpolymer (MW-3,000 daltons) | 0.62% |

Example 16 illustrates a sample two-part solid-layered composition of the invention.

Example 16

| First part | % wt. of first part |
|---|---|
| Calcium hypochlorite | 1.0% |
| Sodium carbonate | 35.9% |
| Succinic acid | 47.7% |
| Sodium polyacrylate (MW-5,100 daltons) | 4.1% |
| Microcrystalline cellulose | 4.1% |
| Laponite RD | 7.2% |
| **Second part** | **% wt. of second part** |
| Sodium bicarbonate | 47.2% |
| Blue Dye | 0.01% |
| Succinic acid | 38.6 |
| Sodium polyacrylate (MW-2,800 daltons) | 4.2% |
| Hydroxypropyl cellulose | 0.8% |
| Laponite RD | 0.8% |
| Frgrance | 0.1% |
| Cross-linked sodium carboxymethylceullose | 4.2% |
| Dodecyl benzene sulfonic acid | 0.58% |
| Sodium sulfate | 3.51% |

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

We claim:

1. A solid-layered bleach composition having at least two parts comprising a first part and a second part:

wherein said first part comprises, a) 0.1%-50% by weight of a hypochlorite selected from the group consisting of calcium hypochlorite, magnesium hypochlorite and mixtures thereof;

b) 20%-60% by weight of a builder selected from carbonate, bicarbonate, sesquicarbonate and mixtures thereof;

c) 0.1%-60% by weight of a water-soluble polymer, wherein said water-soluble polymer is selected from the group consisting of a polycarboxylate, sulfonated carboxylate, polysulfonate, polyvinylpyrrolidone, copolymers and mixtures thereof;

d) 1%-50% by weight of an acid selected from the group consisting of sulfonic acid, dicarboxylic acid, monocarboxylic acid, aminocarboxylic acid and mixtures thereof;

e) optionally, fillers, desiccants, solid processing aids, colorants, a water-swellable polymer wherein said water-swellable polymer is selected from the group consisting of cross-linked polycarboxylate, cross-linked polysulfonate, cross-linked carboxymethyl cellulose, cellulose, sodium carboxymethylcellulose, and mixtures thereof; and f) wherein said first part does not contain sodium hypochlorite, lithium hypochlorite, potassium hypochlorite, hydantoins, isocyanurates, carboxylic acids that have one or more hydroxyl group moieties, aliphatic or aromatic amines that possess a covalently bound proton to the nitrogen moiety, and mixtures thereof; and wherein said second part comprises, a) 0.01%-25% by weight of a surfactant selected from the group consisting of anionic, cationic, nonionic, amphoteric, zwitterionic and mixtures thereof;

b) 10-90% by weight of a builder selected from carbonate, bicarbonate, sesquicarbonate and mixtures thereof;

c) 1-50% by weight of an acid selected from the group consisting of sulfonic acid, dicarboxylic acid, monocarboxylic acid, aminocarboxylic acid and mixtures thereof;

d) optionally dyes, fillers, desiccants, solid processing aids, fragrances, preservatives, colorants, anti-corrosion inhibitors, and mixtures thereof; and e) wherein said second part does not contain any oxidant wherein said oxidant comprises hypochlorite, N-halo compound, peracid, peroxide, peroxygen bleach and mixtures thereof.

2. The composition of claim 1, wherein the composition is in the form of a tablet.

3. The composition of claim 1, wherein the composition is in the form of a granule.

4. The composition of claim 1, wherein the hypochlorite is a calcium hypochlorite.

5. The composition of claim 4, wherein said water-soluble polymer is a polycarboxylate.

6. The composition of claim 5, wherein the polycarboxylate is selected from the group consisting of acrylic, methacrylic, maleic and mixtures thereof.

7. The composition of claim 6, wherein the molecular weight of the polycarboxylate is between 1,000-6,000 daltons.

8. The composition if claim 6, wherein the acid in the first part and second part is a dicarboxylic acid.

9. The composition of claim 8, wherein the first part requires a water-swellable polymer.

10. The composition of claim 8, wherein the surfactant is an anionic surfactant.

11. The composition of claim 10, wherein the second part also requires a water-soluble polymer wherein said water-soluble polymer is selected from the group consisting of a polycarboxylate, sulfonated carboxylate, polysulfonate, polyvinylpyrrolidone, copolymers and mixtures thereof.

12. The composition of claim 11, wherein the composition requires a third part wherein said third part is situated between the first part and second part and said third part comprises a component selected from the group consisting of binder, filler, colorant, desiccant, solid processing aids, sodium chloride, sodium silicate, sodium sulfate, magnesium sulfate, magnesium carbonate, calcium carbonate, calcium hydroxide, calcium oxide, magnesium oxide, magnesium hydroxide, sodium carbonate, potassium carbonate, sodium bicarbonate, sodium sesquicarbonate, potassium sesquicarbonate, sodium borate, boric acid, aluminum hydroxide, silica and mixtures thereof.

13. A solid-layered composition having at least two parts consisting essentially of a first part and a second part:

wherein said first part consisting essentially of, a) 0.1%-50% by weight of a hypochlorite selected calcium hypochlorite, magnesium hypochlorite and mixtures thereof;

b) 20%-60% by weight of a builder selected from carbonate, bicarbonate, sesquicarbonate and mixtures thereof;

c) 0.1%-60% by weight of a water-soluble polymer, wherein said water-soluble polymer is selected from the group consisting of a polycarboxylate, sulfonated carboxylate, polysulfonate, polyvinylpyrrolidone, copolymers, and mixtures thereof;

d) 1%-50% by weight of an acid selected from the group consisting of sulfonic acid, dicarboxylic acid, monocarboxylic acid, amino carboxylic acid and mixtures thereof;

e) optionally, fillers, desiccants, solid processing aids, colorants, a water-swellable polymer wherein said water-swellable polymer is selected from the group consisting of cross-linked polycarboxylate, cross-linked polysulfonate, cross-linked carboxymethyl cellulose, cellulose, sodium carboxymethylcellulose, and mixtures thereof; and f) wherein said first part does not contain sodium hypochlorite, lithium hypochlorite, potassium hypochlorite, hydantoins, isocyanurates, carboxylic acids that have one or more hydroxyl group moiety, aliphatic or aromatic amine that possess a covalently bound proton to the nitrogen moiety, and mixtures thereof; and wherein said second part consisting essentially of, a) 0.01%-25% by weight of a surfactant selected from the group consisting of anionic, cationic, nonionic, amphoteric, zwitterionic and mixtures thereof;

b) 10-90% by weight of a builder selected from carbonate, bicarbonate, sesquicarbonate and mixtures thereof;

c) 1-50% by weight of an acid selected from the group consisting of sulfonic acid, dicarboxylic acid, monocarboxylic acid, aminocarboxylic acid and mixtures thereof;

d) optionally, a water-soluble polymer, wherein said water-soluble polymer is selected from the group consisting of a polycarboxylate, sulfonated carboxylate, polysulfonate, polyvinylpyrrolidone, copolymers and mixtures thereof;

e) optionally, a water-swellable polymer wherein said water-swellable polymer is selected from the group consisting of cross-linked polycarboxylate, cross-linked polysulfonate, cross-linked carboxymethyl cellulose, cellulose, sodium carboxymethylcellulose, and mixtures thereof;

f) optionally dyes, fillers, desiccants, solid processing aids, fragrances, preservatives, colorants, anti-corrosion inhibitors, and mixtures thereof; and g) wherein said second part does not contain any oxidant wherein said oxidant comprises hypochlorite, N-halo compound, peracid, peroxide, peroxygen bleach and mixtures thereof.

14. The composition of claim 13, wherein the water-soluble polymer is a polycarboxylate and the acid in the first and second part is a dicarboxylic acid.

15. The composition of claim 14, wherein the hypochlorite is calcium hypochlorite and the surfactant is anionic.

16. The composition of claim 15, wherein the first part requires a water-swellable polymer.

17. The composition of claim 16, wherein the second part requires a water-soluble polymer.

18. The composition of claim 17, wherein the second part requires a water-swellable polymer.

19. The composition of claim 18, wherein the composition requires a third part wherein said third part is situated between the first part and second part and said third part comprises a component selected from the group consisting of binder, filler, colorant, desiccant, sodium chloride, sodium silicate, sodium sulfate, magnesium sulfate, magnesium carbonate, calcium carbonate, calcium hydroxide, calcium oxide, magnesium oxide, magnesium hydroxide, sodium carbonate, potassium carbonate, sodium bicarbonate, sodium sesquicarbonate, potassium sesquicarbonate, sodium borate, boric acid, aluminum hydroxide, silica and mixtures thereof.

20. A solid-layered composition having at least two parts consisting of a first part and a second part:

wherein said first part consisting of, a) 0.1%-50% by weight of a hypochlorite selected from the group consisting of calcium hypochlorite, magnesium hypochlorite and mixtures thereof;

b) 20%-60% by weight of a builder selected from carbonate, bicarbonate, sesquicarbonate and mixtures thereof;

c) 0.1%-60% by weight of a water-soluble polymer, wherein said water-soluble polymer is selected from the group consisting of a polycarboxylate, sulfonated carboxylate, polysulfonate, polyvinylpyrrolidone, copolymers and mixtures thereof;

d) optionally, fillers, desiccants, solid processing aids, colorants, a water-swellable polymer wherein said water-swellable polymer is selected from the group consisting of cross-linked polycarboxylate, cross-linked polysulfonate, cross-linked carboxymethyl cellulose, cellulose, sodium carboxymethylcellulose, and mixtures thereof; and e) wherein said first part does not contain sodium hypochlorite, lithium hypochlorite, potassium hypochlorite, hydantoins, isocyanurates, carboxylic acids that have one or more hydroxyl group moieties, aliphatic or aromatic amines that possess a covalently bound proton to the nitrogen moiety, and mixtures thereof; and wherein said second part consisting of, a) 0.01%-25% by weight of a surfactant selected from the group consisting of anionic, cationic, nonionic, amphoteric, zwitterionic and mixtures thereof;

b) 10-90% by weight of a builder selected from carbonate, bicarbonate, sesquicarbonate and mixtures thereof;

c) optionally dyes, fillers, desiccants, solid processing aids, fragrances, preservatives, colorants, anti-corrosion inhibitors, a water-swellable polymer wherein said water-swellable polymer is selected from the group consisting of cross-linked polycarboxylate, cross-linked polysulfonate, cross-linked carboxymethyl cellulose, cellulose, sodium carboxymethylcellulose, and mixtures thereof; and d) wherein said second part does not contain any oxidant wherein said oxidant comprises hypochlorite, N-halo compound, peroxygen bleach and mixtures thereof.

* * * * *